United States Patent [19]

Yates, Jr. et al.

[11] Patent Number: 4,663,297

[45] Date of Patent: May 5, 1987

[54] TEMPERATURE PROGRAMMED SPECTROSCOPY TECHNIQUES

[76] Inventors: John T. Yates, Jr.; Gregory L. Griffin; Maya Kiskinova, all of c/o Dept. of Chemical Engr. & Materials Science, University of Minnesota, Minneapolis, Minn. 55455

[21] Appl. No.: 416,666

[22] Filed: Sep. 10, 1982

[51] Int. Cl.$^4$ .................... G01N 15/00; G01N 37/00
[52] U.S. Cl. .................................. 436/147; 436/37
[58] Field of Search ............... 73/19; 250/281, 282, 250/288; 374/14, 54; 436/5, 7, 37, 148, 147, 182, 183; 324/71.5, 468, 469; 422/94, 95, 98, 88; 55/20; 34/26

[56] References Cited

U.S. PATENT DOCUMENTS

| | | | |
|---|---|---|---|
| 2,742,585 | 4/1956 | Zemany | 324/468 X |
| 3,610,023 | 10/1971 | Ageikin et al. | |
| 3,852,037 | 12/1974 | Kolb et al. | 422/54 |
| 4,025,605 | 5/1977 | Dalton, Jr. et al. | |
| 4,170,901 | 10/1979 | Conkle et al. | |
| 4,224,595 | 9/1980 | Dolan | 422/88 X |
| 4,305,724 | 12/1981 | Micko | 422/94 X |
| 4,327,054 | 4/1982 | Yasuda et al. | 73/27 R X |
| 4,399,684 | 8/1983 | Advani et al. | 73/1 G |

FOREIGN PATENT DOCUMENTS

| | | | |
|---|---|---|---|
| 494778 | 3/1976 | Australia | 324/71.5 |
| 55-83845 | 6/1980 | Japan | 422/94 |
| 2013901 | 8/1979 | United Kingdom | 422/94 |

OTHER PUBLICATIONS

Yates, Jr; Methods in Experimental Physics, Academic Press, New York, N.Y. 1978.
Barrer, R. M., and Sutherland, J. W., Proc. Roy., Soc. Ser., A 237, 439 (1956).
Barrer, R. M., Bultitude, F. W., and Sutherland, J. W., Trans Faraday Soc., 53, 111(1957).
Redhead, P. A., Vacuum 12, 203(1962).
Cvetanovic, R. J., and Amenomiya, Y., in "Advances in Catalysis and Related Subjects", vol. 17, p. 103, Academic Press, New York/London, 1967.
Bezus, A. G., Kiselev, A. V., Sedlacek, Z., and Du, P. Q., J. Chem. Soc. Faraday Trans., 67, 468 (1971).
King, D. A., Madey, T. E., and Yates, J. T., Jr., J. Chem. Phys., 55, 3236(1971); 55, 3247(1971).
Baranski, A., Ceckiewicz, S., and Caluszka, J., Bull. Acad. Pol. Sci. Ser. Sci., Chim. 24, 645(1976).
Iwamoto, M., Maruyama, K., Yamazoe, N., and Seiyama, T., J. Phys. Chem., 81, 622(1976).
Chan, Y. C., and Anderson, R. B., J. Catal., 50, 319(1977).
Doelle, H. S., and Riekert, L., in "Molecular Sieves—II" (J. R. Katzer, Ed.), p. 401, ACS Symposium Series No. 40, Amer. Chem. Soc., Washington, D.C., 1977.
Rudham, R., and Stockwell, A., in "Catalysis—vol. 1" (Specialist Periodic Reports), (D. A. Dowden, Ed.), p. 87, The Chemical Society, London, 1977.
Rabo, J. A., Bezman, R. D., and Poutsma, M. L., Acta Phys. Chem. 24, 39(1978).
Harlfinger, R., Hoppach, D., Hofman, H. P., and Quitzsch, K., Z. Phys. Chem. Leipzig, 260, 905 (1979).
Gorte, "Design Parameters for Temperature Programmed Desorption from Porous Catalysts, Journal of Catalysis, 75, pp. 164–174 (1982).
Yates, Jr., "The Thermal Desorption of Adsorbed Species", Methods of Experimental Physics, vol. 22, pp. 425-464 (1985).
Kishinova et al., "Thermal Desorption Spectroscopy from High-Specific-Area Solids . . . , Journal of Catalysis, vol. 71, pp. 278-287, Oct. 1981.
Brenner et al., "Experimental Errors in the Application of Temperature-Programmed Desorption to Practical Catalysts, Journal of Catalysis, vol. 56, pp. 134-138 (1979).
Konvalinka et al., "Temperature Programmed Desorption of Hydrogen from Nickel Catalysts, Applied Catalysis, vol. 1, pp. 141-158 (1981).

Primary Examiner—Barry S. Richman
Assistant Examiner—Michael S. Gzybowski
Attorney, Agent, or Firm—Majestic, Gallagher, Parsons & Siebert

[57] ABSTRACT

Temperature programmed spectroscopy wherein particles of a substrate under investigation are attached in a non-overlapping manner to a heating filament. The temperature of the filament is increased in a controlled manner, thus increasing the temperature of the attached substrate particles as well. An instrument for analyzing the gases is a mass spectrometer. Gases desorbed from the particles can be studied according to this technique, or the nature of heterogeneous catalytic chemical reactions of a gaseous atmosphere on the particles' surface may alternatively be detected and studied.

16 Claims, 4 Drawing Figures

TEMPERATURE PROGRAMMED SPECTROSCOPY TECHNIQUES

RIGHTS OF THE U.S. GOVERNMENT

The invention described herein may be manufactured and used by or for the Government of the United States without the payment of any royalties thereon or therefor.

BACKGROUND OF THE INVENTION

This invention is related to the art of kinetic spectroscopy wherein gases either desorbed from or resulting from a catalytic reaction on a substrate surface are detected as a function of the temperature of the surface, generally referred to as temperature programmed desorption spectroscopy.

The art of thermal desorption spectroscopy is primarily directed to the study of substrate surfaces by analyzing the characteristics of desorption of controlled gaseous molecules from the surface. When a solid surface is exposed to gaseous molecular species, the species often form an adsorbed layer on the solid surface. The molecules adhere to the surface by either chemical or physical bonds. The high area substrate material is often in the form of small particles which are held in a bed of particles. The temperature of this bed is gradually increased in a vacuum or carrier gas environment. Gases desorbed from the surface area of these particles are analyzed by instruments such as a gas chromatograph or a mass spectrometer. The desired information output is the change in partial pressure in the desorbed gas as a function of the temperature of the bed of substrate particles. Peaks in differential partial pressure occur at different bed temperatures, providing information on the characteristics, including composition, of the substrate particle surface as it interacts with the adsorbed species under investigation.

There are certain recognized limitations of this technique. One such limitation is that diffusion through the bed of particles may interfere with measurements of desorption rates. That is, gas molecules desorbed from one particle may be adsorbed by another and then again desorbed before escaping the bed of particles and reaching the gas analyzer. Another difficulty is maintaining the temperature of all particles in the bed at the same temperature as the temperature is programmed upwards. The undesired result of these two factors is that the output data is blurred; that is, the desired sharp peaks of differential partial pressure do not appear but rather are blurred together.

The approach taken by existing technology is to extract the desired peak information from the blurred output data. This involves complicated computer implemented processing of that data. It is a principal object of the present invention to provide a technique for measuring the desired desorption peaks in a simpler and more accurate way.

It is a further object of the present invention to provide a system and general technique for all types of temperature programmed spectroscopy, including, in addition, the investigation of catalytic reaction chemistry, pore diffusion in porous substrate materials, and catalyst preparation using hydrogen or other gaseous reducing agents.

SUMMARY OF THE INVENTION

These and additional objects are accomplished by the various aspects of the present invention wherein, briefly, the substrate particles are spread out and held in a substantially non-overlapping manner over a surface whose temperature is raised in a controlled manner. A preferred surface is that of an electrically heated filament whose surface is inert. The temperature of all of the substrate particles supported by the filament is easily maintained uniform as the filament temperature is raised as a function of time. Diffusion of gases between particles is minimized and substantially eliminated by spreading the particles out, away from each other.

When using this arrangement for thermal desorption spectroscopic studies of the substrate particle surfaces, molecules of a gas of interest, previously adsorbed onto the surface of the substrate particles, are desorbed from those surfaces as the temperature of the electrical filament is raised by controllably increasing the electrical current through the filament. The desorption peaks are directly measured are sharp and no complicated processing of the measured data is necessary to extract the desired information from these peaks. The desorption measurement process is accomplished at a very low pressure within an appropriate chamber and the preferred gas detector is a very sensitive quadrupole mass spectrometer.

Other studies can also be accomplished by using the arrangement of substrate particles spread out over a controllably heated surface, according to another aspect of the invention. For example, catalytic reactions of gases with the substrate surfaces may be studied by introducing, into a chamber containing the substrate particles, reactant gases at around atmospheric pressure. Gaseous products of the reaction are removed from the chamber by a very small orifice and analyzed as a function of the filament temperature.

The applicants herein have published many details of their invention in an article appearing in the October, 1981 issue of *Journal of Catalysis*, Volume 71, pages 278-287. That paper is expressly incorporated herein by reference.

Additional objects, advantages and features of the various aspects of the present invention are included in the following description of their preferred embodiments, which description should be taken in conjunction with the accompanying drawings.

DESCRIPTION OF THE PREFERRED EMBODIMENTS

Figure 1:
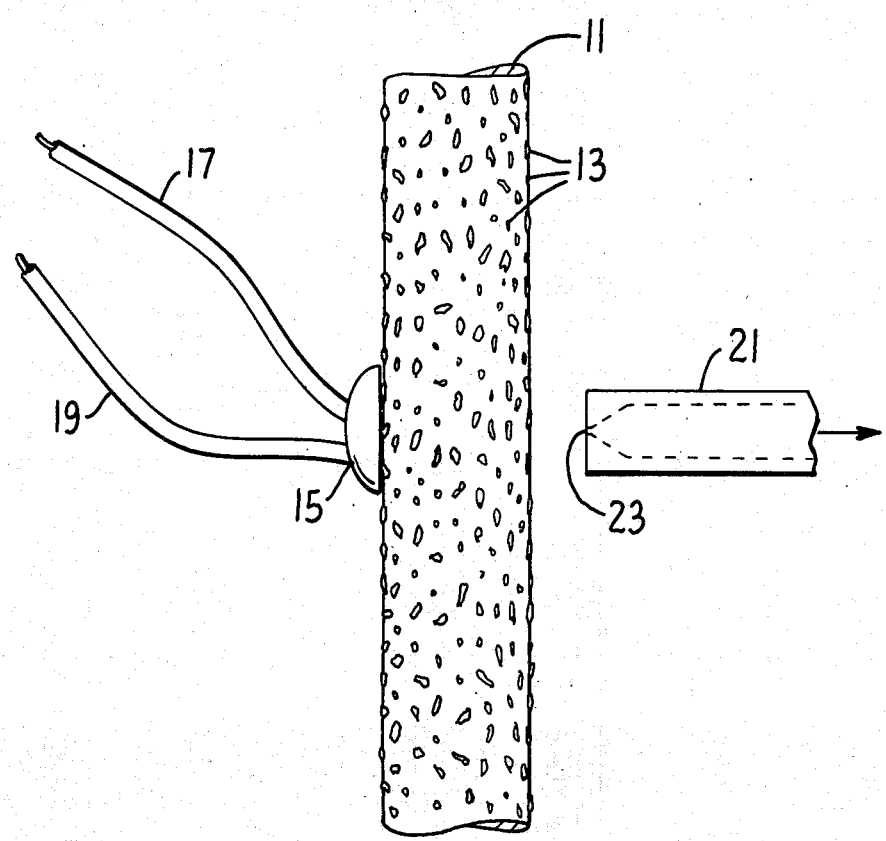
FIG. 1 is an enlarged view of a plurality of substrate particles attached to a heated surface.

Referring to FIG. 1, an electrical filament of circular cross-section is shown many times enlarged. A thermocouple 15 is welded to one point along the length of the filament 11, and carries information as to the temperature of that point over wires 17 and 19. Attached to the filament's surface near the thermocouple 15 are a large number of small particles 13 of a desired substrate material or materials to be investigated. A small tube 21 is positioned so that a tiny orifice 23 at its end is very close to the surface of the filament 11. Its purpose is to sample gases from a region adjacent to filament 11 for introduction to the mass spectrometer analyzer, as better shown in FIGS. 3 and 4, when catalytic reactions of the substrate are being studied in a gas phase environment. The sampling tube 21 can be of the form of a fine capillary tube or a small orifice of small enough size to sample gas at a rate appropriate for the mass spectrometer and the turbopump.

Figure 2:
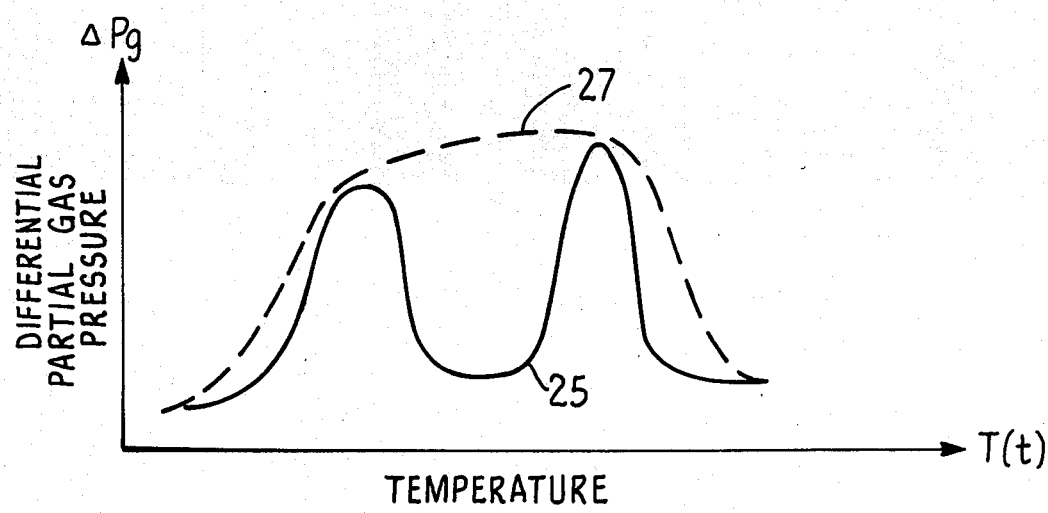
FIG. 2 is a schematic curve illustrating typical results desired from a temperature programmed spectrometer.

Referring to FIG. 2, a curve 25 is given for purposes of explanation to show two sharp peaks which gives information as to the nature and composition of the substrate particles 13. The curve 25 shows the differential partial pressure of gas being desorbed from the surfaces of the particles 13 in a vacuum as a function of the temperature of those particles. The temperature of the particles is gradually raised by increasing the electrical current through the filament 11 in a programmed manner. The two peaks of the curve 25 reveal that there are two different bonding modes for the adsorbed species on the substrate particles' 13 surface. The temperature at which the peaks occur are characteristic of these surface bonding modes. The area of the curve at a peak is proportional to the number of sites of that particular substrate material that hold a molecule of the gas that is analyzed. The gases that are desorbed by this gradual heating of the substrate particles 13 have previously been adsorbed by exposing the particles to the gas.

A blurred peak 27 is shown in dotted outline in FIG. 2 as illustrative of the type of information that is obtained according to present techniques of thermal desorption spectroscopy wherein the particles are held together in a bed or group. As described above, such a distribution of the particles may lead to intergranular diffusion of desorbed gas molecules and an uneven temperature of the substrate particles. This blurring of the data output is corrected, according to the present invention, by correcting the conditions that cause the blurring, rather than attempting to compensate for it by processing the blurred data 27 in order to identify the peaks 25, as is done by others using existing techniques.

The particles 13 can conveniently be attached to the surface of the filament 11 by depositing on a section of the filament a slurry mixture of the particles 13 in a solvent, followed by evaporation of the solvent. Once the filament 11 dries, the particles remain adhered to it. The surface of the filament 11 should be inert; that is, it should not itself give off gas molecules to any substantial degree which would interfere with detecting the gas molecules of particular interest. It has been found that a tungsten filament with its outer surface being lightly oxidized is satisfactory. If there is any substantial amount of undesired gas molecules emitted from the filament, a control filament without substrate particles attached to it can be included as part of any spectrometer in order to determine the component of the output readings due to the filament itself, which components can then be subtracted from the measurements made on the sample filament.

Figure 3:
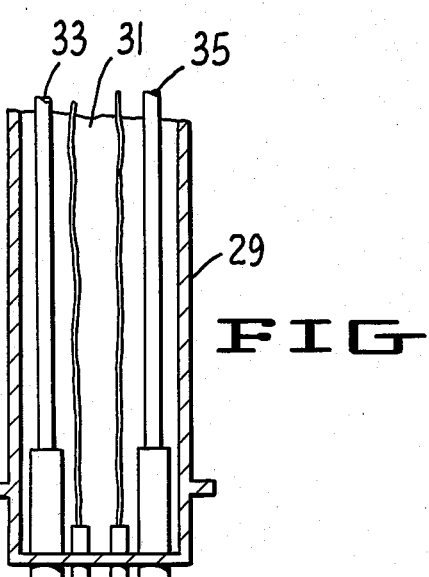
FIG. 3 shows a sub-assembly of such a spectrometer which utilizes the substrate particle holding technique according to FIG. 1.

Referring to FIG. 3, a sub-assembly of a temperature programmed spectrometer is illustrated which uses the system of FIG. 1. A container 29 of a cooling liquid 31 serves to support at its bottom the filament 11 in a loop. The temperature of the cooling liquid serves to define the lower limit of adsorption temperature for the sample. Wires 33 and 35 are connected to opposite ends of the filament 11. As is shown in FIG. 4, the filament energizing conductors 33 and 35 and the thermocouple conductors 17 and 19 are connected to a programmable power supply 37, which may be adjusted to program the filament temperature at various desired rates.

Figure 4:
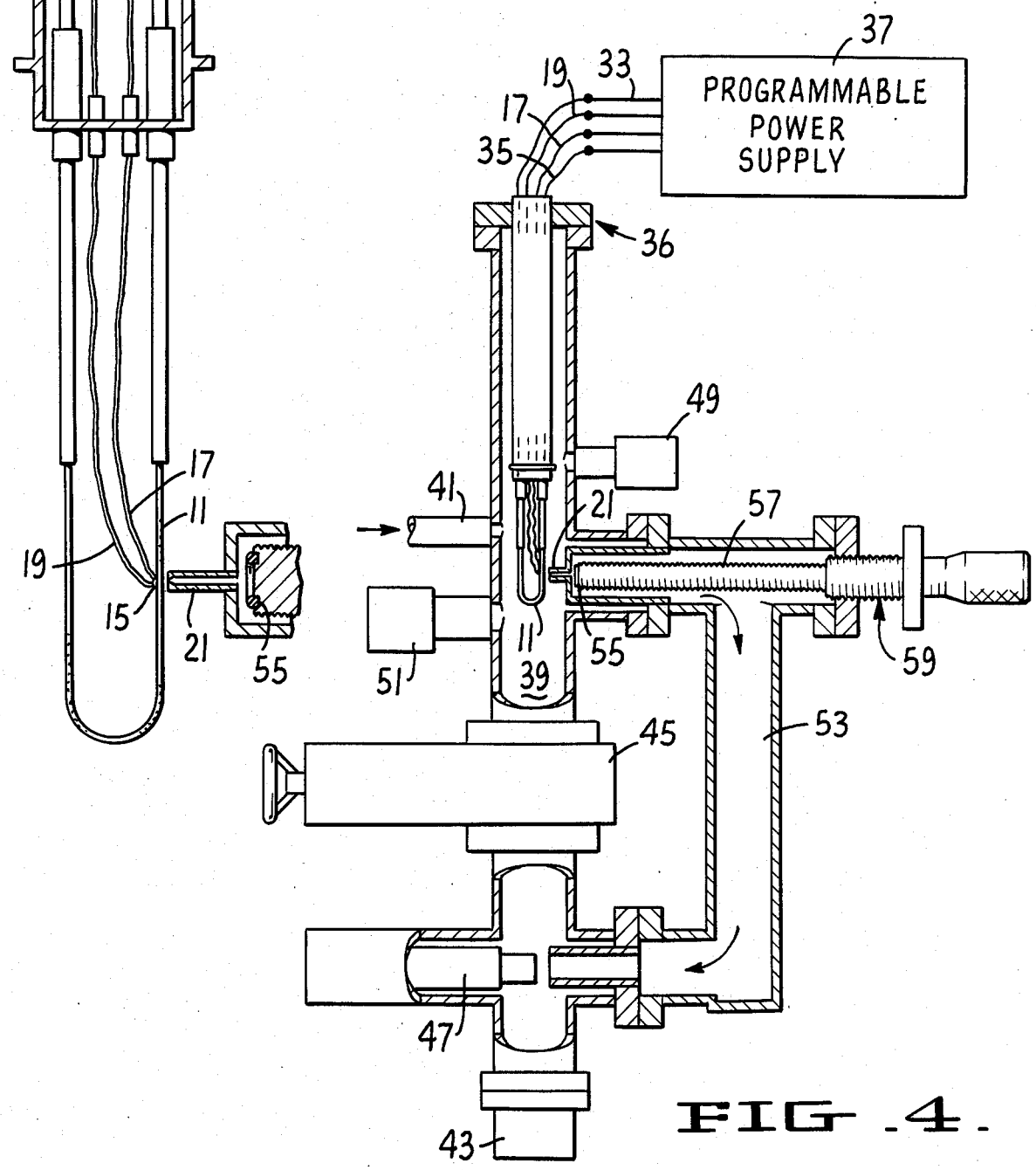
FIG. 4 shows in schematic form the essential elements of a complete spectrometer system which includes the sub-assembly of FIG. 3.

The sub-assembly of FIG. 3, as shown in FIG. 4, is contained within a vacuum chamber 39. The filament sub-assembly may be conveniently removed by opening the support flange assembly 36. The temperature of the filament 11 is raised in a predetermined manner by a programmed electrical current increase through the filament.

The apparatus of FIG. 4 is capable of being used to study either the desorption of gases from the particles or the catalytic reaction of the particle surfaces with the gases, as discussed previously. In either case, a gas inlet tube 41 is provided into the enclosed chamber 39. Gases are admitted into the chamber through the tube 41. When the system of FIG. 4 is being used for desorption spectroscopy, the single gas of interest is first introduced into the chamber so that the particles previously attached to the filament can adsorb the gas on its surfaces. The chamber 39 is then evacuated by the use of a turbopump 43 through a gate valve 45 which is held open during this process. Once the chamber 39 is evacuated, the filament 11 is gradually increased in temperature and gases desorbed from the substrate surfaces are measured by a quadrupole mass spectrometer 47 through the gate valve 45 which is held open. This provides the information previously discussed with respect to FIG. 2 concerning the substrate surface characteristics. Since typical base pressures prior to desorption are very low (less than $1 \times 10^{-8}$ torr), the sensitivity of the mass spectrometer detector is enhanced, permitting very small substrate samples to be employed. The low base pressure is achieved by using materials of construction in the apparatus which have low outgassing rates. The high mass spectrometer sensitivity gives large output signals with a small amount of gas present, and the high vacuum condition of the instrument of FIG. 4 results in an extremely low undesired background signal.

Certain other measuring instruments are connected with the chamber 39. A capacitance manometer 49 is connected to the chamber 39 through an appropriate port. Similarly, a Bayard Alpert gauge 51 is connected through another port to the chamber 39. Also, for many applications, it is desirable to have a transparent window portion in a wall of the chamber 39 so that the geometrical conditions within the chamber can be observed from the outside.

The capillary needle 21 is not utilized when the system of FIG. 4 is used for desorption spectroscopy but when the system is used for high pressure catalytic reaction chemistry with the surfaces of particles attached to the filament 11, gases drawn through the small tube 21 become the source for the mass spectrometer 47 and are applied thereto through a wide bore tabulation 53. A copper focusing insert is provided in the passage 53 on the same axis as mass spectrometer 47 in order to better focus the available gases into the mass spectrometer 47. This increases the efficiency and sensitivity of the instrument. A capillary 21 is opened and closed by a valve formed of an O-ring seal 55 at the end of a linear translation element 57. The element 57 is moved back and forth by a micrometer control assembly 59 of a conventional design. When the linear translation element 57 is pulled away from the small tube 21, its capillary opening then communicates with the mass spectroscopy 47 through the passage 53. This passage is closed off by moving the element 57 so that the seal 55 presses tightly against the surface surrounding the small tube 21. By valving the capillary opening through the tube 21 at this position, there is a very small dead-space volume within the tube and within the O-ring seal that retains gases after it is closed off. A small dead-space volume is desired in order to provide a fast response to the detection of different gases from the reactor chamber 39 at subsequent times. The volume can be reduced even further by a single ball-like resilient element in the center of the end of the longitudinal translator element 57 to replace the O-ring 55 and close off the inner end of the tube 21 directly.

When operating the system of FIG. 4 in its second mode to study the catalytic reaction of gases with substrate particles, the chamber 39 is first evacuated by the turbopump 43 with the gate valve 45 opened. The valve 45 is then closed. Desired gases are introduced into the chamber 39 through the inlet 41 until the desired composition and pressure within the chamber 39 is reached. The filament 11 is then increased in temperature in a programmed manner and the mass spectrometer 47 receives gases through the small tube 21 for analysis without significantly reducing the pressure in the chamber 39. In addition, the system may be operated as a static catalytic reactor by maintaining the filament at a constant temperature sufficient to produce a measurable rate for the catalytic reaction.

It will be recognized that the system of FIG. 4 and the techniques described above can be used in a wide range of chemical processes at the surface of high specific area solids. Among them is the study of adsorption/desorption processes, the investigation of catalytic reaction chemistry, the investigation of pore diffusion in zeolites and other porous materials, and the investigation of catalyst preparation using hydrogen or other gaseous reducing agents.

Although the various aspects of the present invention have been described with respect to its preferred embodiments, it will be understood that the invention is entitled to protection within the full scope of the appended claims.

It is claimed:

1. A method of measuring the rate of desorption of gases from a substrate surface, comprising the steps of:
arranging a plurality of small particles of said substrate in a substantially non-overlapping manner along a surface of material that is characterized by being substantially chemically inert,
raising the temperature of said material in a controlled manner as a function of time, and
detecting as a function of temperature of said material, the rate of desorption of gases from surfaces of said substrate particles by measuring the desorbing gases themselves, whereby characteristics of said substrate particle surfaces may be determined.

2. A method of thermal desorption spectroscopy, comprising the steps of:
arranging particles of a substrate in a substantially non-overlapping manner along a surface of an electrically resistive filament made of a material that is characterized by being substantially chemically inert,
raising the temperature of said filament in a controlled manner as a function of time by applying a gradually increasing electrical current therethrough, and
detecting, as a function of filament temperature, the rate of desorption of gases from surfaces of said substrate particles by measuring the desorbing gases themselves, whereby characteristics of said substrate particle surfaces may be determined.

3. The method of claim 2 wherein said particles are spaced along the filament surface in a manner such that substantially no gases desorbed from one particle are adsorbed by another particle.

4. A method of thermal desorption spectroscopy, comprising the steps of:
arranging particles of a substrate in a substantially non-overlapping manner on a surface of a material that is characterized by being substantially chemically inert,
positioning said material in a vacuum chamber and reducing air pressure therein to a very low level,
raising the temperature of said material in a controlled manner, and
detecting, as a function of the temperature of said material, the rate of desorption of gases from surfaces of said substrate particles by measuring the desorbing gases themselves, whereby characteristics of said substrate particle surfaces may be determined.

5. The method of claim 4 which additionally includes, prior to heating said material, the step of exposing the particle coated material to a selected gas, whereby molecules of said gas are adsorbed by said substrate particles for the subsequent desorption step.

6. The method of claim 4 wherein said material includes a filament element made of tungsten whose surface is oxidized.

7. The method of claim 4 wherein said particles are spaced far enough apart from each other along said material surface so that substantially no gases desorbed from one particle are adsorbed by another particle.

8. The method of any of claims 4, 5, 6 or 7 wherein the detecting step is accomplished by a mass spectrometer instrument which is connected to said vacuum chamber.

9. The method of claim 4 wherein the step of arranging particles includes the step of positioning said particles on a surface of a material that comprises an electrically resistive wire filament, and wherein the step of raising the temperature of the material includes applying a gradually increasing electrical current therethrough.

10. The method of any of claims 2 3 or 9 wherein the step of arranging particles of a substrate on a filament includes the steps of depositing on said filament a slurry mixture of said particles in a solvent, and allowing evaporation of said solvent.

11. A method of detecting gaseous products of a catalytic reaction with a substrate surface, comprising the steps of:
arranging a plurality of small particles of said substrate in a substantially non-overlapping manner along a surface of material that is characterized by being substantially chemically inert,
surrounding the particle layered surface with a desired gaseous mixture,
raising the temperature of said material in a controlled manner as a function of time, and detecting, as a function of the temperature of said material, the composition of gases surrounding said heated, particle layered surface, whereby the nature of any catalytic reaction between said desired gaseous mixture and surfaces of said substrate particles are determined and characteristics of said substrate particle surfaces may be determined.

12. The method of claim 11 wherein the step of arranging the small particles of substrate on a surface of material includes the step of arranging said particles on a surface of an electrically resistive filament, and wherein the step of raising the temperature of the material includes the step of increasing an electrical current flowing through the filament.

13. The method of either claim 11 or 12 wherein the material heating step is accomplished with the desired gaseous mixture being maintained at a pressure of approximately one atmosphere or higher, and wherein the gas detection step includes sampling gases from said surface through a small capillary tube positioned with an end opening adjacent said particle layered surface, said sampled gases being fed to a mass sepctrometer.

14. The method of any of claims 1, 4, 5, or 12 wherein the step of arranging particles of a substrate on said surface of material includes the steps of depositing on said surface a slurry mixture of said particles in a solvent, and allowing evaporation of said solvent.

15. The method of any of claims 1, 2, 4, 5, 6, 11 or 12 wherein the detecting step includes measuring the partial pressure of the desorbing gases.

16. The method of any of claims 1, 2, 3, 4, 11 or 12 wherein the detecting step includes passing the desorbing gases into a mass spectrometer.

* * * * *

UNITED STATES PATENT AND TRADEMARK OFFICE
CERTIFICATE OF CORRECTION

PATENT NO. : 4,663,297
DATED : May 5, 1987
INVENTOR(S) : Yates, Jr., et al.

It is certified that error appears in the above-identified patent and that said Letters Patent is hereby corrected as shown below:

Col. 5, line 57:   insert --,-- after "detecting";

Col. 6, line 53:   insert --,-- after "claim 2";

Col. 8, line 5:    "sepctrometer" should be --spectrometer--; and

Col. 8, line 6:    insert --11,-- between "5," and "or 12".

Signed and Sealed this

Nineteenth Day of January, 1988

Attest:

DONALD J. QUIGG

*Attesting Officer*   *Commissioner of Patents and Trademarks*